United States Patent [19]
Deckers et al.

[11] Patent Number: 5,498,796
[45] Date of Patent: Mar. 12, 1996

[54] PROCESS FOR THE PREPARATION OF AMINES BY CATALYTIC HYDROGENATION OF NITRILES

[75] Inventors: Gregor Deckers, Xanten; Dieter Frohning, Wesel, both of Germany

[73] Assignee: Hoechst Aktiengesellschaft, Germany

[21] Appl. No.: 426,142

[22] Filed: Apr. 19, 1995

Related U.S. Application Data

[63] Continuation of Ser. No. 259,117, Jun. 10, 1994, abandoned, which is a continuation of Ser. No. 990,730, Dec. 15, 1992, abandoned.

[30] Foreign Application Priority Data

Dec. 18, 1991 [DE] Germany .................... 41 41 771.2

[51] Int. Cl.$^6$ ................................. C07C 209/48
[52] U.S. Cl. ................ 564/493; 502/328; 564/415
[58] Field of Search .................... 564/493, 511, 564/415, 490; 502/328

[56] References Cited

FOREIGN PATENT DOCUMENTS

| 322049 | 6/1989 | European Pat. Off. ......... B01J 23/74 |
| 340848 | 11/1989 | European Pat. Off. ............... 564/493 |
| 384542 | 8/1990 | European Pat. Off. ...... C07C 209/48 |
| 398668 | 11/1990 | European Pat. Off. ......... B01J 23/74 |
| 472918 | 3/1992 | European Pat. Off. ......... B01J 23/74 |
| 490382 | 6/1992 | European Pat. Off. ............... 564/493 |

*Primary Examiner*—Brian M. Burn
*Attorney, Agent, or Firm*—Bierman and Muserlian

[57] ABSTRACT

A process for the preparation of amines by catalytic hydrogenation of nitriles in the presence of a nickel-containing support catalyst. The support catalyst contains Mg and Ni in coprecipitated form and in a molar ratio of 0.0075 to 0.075:1. There is 17 to 60 g of a water-insoluble support per mol of nickel, and 65% to 97% of the BET total surface area of the support catalyst is formed by pores having a radius $r_p \leq 2.5$ nm.

30 Claims, No Drawings

PROCESS FOR THE PREPARATION OF AMINES BY CATALYTIC HYDROGENATION OF NITRILES

This application is a continuation of application Ser. No. 08/259,117 filed Jun. 10, 1994, now abandoned, which is a continuation of Ser. No. 07/990,730, filed Dec. 15, 1992, now abandoned.

This Application claims the benefit of priority of German Application 41 41 771.2, filed Dec. 18, 1991.

The present invention relates to a process for preparing amines by catalytic hydrogenation of nitriles in the presence of a nickel-containing, supported catalyst. The catalytic hydrogenation of nitriles, in particular saturated or unsaturated fatty acid nitriles, leads to the corresponding saturated or unsaturated primary or secondary amines, depending on the starting material and the reaction conditions selected in each case.

BACKGROUND OF THE INVENTION

EP 384 542 describes a process for preparing secondary alkylamines by catalytic hydrogenation in the presence of a nickel-containing catalyst which contains copper, and optionally cobalt as a promoter.

DE 39 14 875 C2 relates to a process for the catalytic hydrogenation of aliphatic nitriles to amines using a nickel catalyst on a support containing magnesium oxide and silicon dioxide. The catalyst has a molar ratio of silicon dioxide to nickel of between 0.1 and 0.3 and a molar ratio of magnesium to nickel of between 0.25 and 0.05, as well as an average pore radius of 1.5 to 4.0 nm.

However, despite comparatively good hydrogenation results, the state-of-the-art processes generally have some weaknesses, including (1) the reaction conditions (pressure, temperature), (2) the activity of the catalyst used for hydrogenation, (3) the filterability of the catalyst, and (4) the selectivity of the reaction. Furthermore, it is desirable to have a process with a wide range of applications which makes it possible to prepare, as desired, a saturated primary amine, a saturated secondary amine, or an unsaturated primary amine, in high yields.

SUMMARY OF THE INVENTION

This problem is solved by a process for preparing amines by catalytic hydrogenation of nitriles in the presence of a nickel-containing supported catalyst, with the optional addition of ammonia, at elevated temperature and optionally at elevated pressure.

Such catalysts have the following characteristics:

(1) Mg and Ni are present in coprecipitated form
(2) The molar ratio of Mg to Ni is 0.0075–0.075:1
(3) There is 17 to 60 g of water-insoluble support per mol of Ni
(4) The active Ni metal surface is 110 to 180 $m^2/g$ of Ni
(5) 65% to 97% of the BET total surface area of the catalyst is formed by pores of radius $r_p \leq 2.5$ nm.

A major feature of the inventive support catalyst is the narrow distribution of pore radii, indicated by a high proportion of the BET total surface area being attributable to pores having a radius $r_p \leq 2.5$ nm. The BET total surface area is 160 to 450, in particular 180 to 380, preferably 200 to 350, $m^2/g$ of catalyst. The $m^2$ BET total surface area is understood to mean the surface area determined by the adsorption of nitrogen according to the Brunauer, Emmett and Teller (BET) method which is described in the J. Amer. Chem. Soc. 60., (1938) page 309. As a result of the aforementioned narrow distribution of pore radii (limited to $r_p \leq 2.5$ nm), the catalyst gains certain special properties which lead to an increase in activity and an improvement in the selectivity of the reaction which form the basis of the present invention.

DETAILED DESCRIPTION OF THE INVENTION

A feature of the catalyst is its composition, indicated by the molar ratio of Mg to Ni. As previously mentioned, in reduced form, the catalyst contains Mg and Ni in a molar ratio of 0.0075 to 0.075:1. It has proven particularly successful to select a molar ratio of Mg:Ni of 0.015 to 0.060:1, more preferably 0.022 to 0.055:1. 1 mol of Mg or 1 mol of $Mg^{2+}$ corresponds to 24.305 g of Mg or 24.305 g of $Mg^{2+}$, and 1 mol of Ni or 1 mol of $Ni^{2+}$ corresponds to 58.71 g of Ni or 58.71 g of $Ni^{2+}$. When the catalyst is in its reduced state, the magnesium is present as $Mg^{2+}$ and the nickel mainly or almost completely in metallic form. The definition of the molar ratio is precisely worded as the ratio of mols of $Mg^{2+}$:(mol of Ni+mol of unreduced $Ni^{2+}$).

The composition of the novel catalyst is further defined by the ratio of the parts by weight of the water-insoluble support to nickel, the term nickel again being understood to mean the sum of the mols of metallic nickel and the mols of $Ni^{2+}$.

Various water-insoluble materials are suitable as supports. These include silicates, such as calcium, magnesium and/or aluminium silicates; $Al_2O_3$; $SiO_2$; and/or kieselguhr. Magnesium silicates (especially in the form of pumice), $Al_2O_3$, and/or kieselgur, are especially useful. Pumice, $Al_2O_3$, $SiO_2$, and/or kieselguhr are preferred and $SiO_2$ and/or kieselguhr deserve special mention as being most preferred. Kieselguhr has proven particularly successful.

The support material should normally be present in the form of fine particles. Its particles should exhibit a grain size of 1 to 30, in particular 2 to 25, preferably 3 to 20 μm. The catalyst contains 17.0 to 60.0, in particular 25 to 50, preferably 30 to 40 g of support per mol of Ni. As already mentioned herein, moles of nickel is understood to mean the total nickel in both reduced and unreduced form. The active nickel metal surface area of the catalyst is 110 to 180, in particular 125 to 160, preferably 130 to 150 $m^2/g$ of nickel. It is determined on the basis of a method described in the Journal of Catalysis 81, (1983) page 204 and 96, (1985) page 517 by measurement of the amount of hydrogen chemisorbed at 20° C.

Of the BET total surface area, 65% to 97%, in particular 70% to 95%, preferably 75% to 95% is formed by pores having a radius $r_p \leq 2.5$ nm (25 Å). Moreover, it is a further improvement that 60% to 95%, in particular 70% to 95%, preferably 73% to 90%, or the BET total surface area is formed by pores having a radius $r_p$ of 1.5 to 2.5 nm (15 to 25 Å). It is more advantageous if pores having a radius $r_p$ of 1.8 to 2.5 nm (18 to 25 Å) form 35% to 85%, in particular 45% to 76%, preferably 50% to 70% of the BET total surface area. The pore radii are determined according to a method described in Adsorption Surface Area and Porosity by S. J. Gregg and K. S. W. Sing (Academic Press New York-London 1967), pages 160 to 182.

The process for preparing the catalyst starts with an aqueous solution containing nickel and magnesium salts. This mixed salt solution contains 10 to 100, in particular 20 to 80, preferably 30 to 50 g of Ni/liter. It exhibits magnesium corresponding to 0.2 to 15, in particular 0.5 to 12, preferably 1 to 10 g of MgO/liter.

The mixed salt solution is prepared by dissolving water-soluble, inorganic, organic, or complex salts of nickel and magnesium in water. Well-suited salts are the sulfates, chlorides, acetates, propionates, butyrates, and nitrates. It has proven particularly successful to use nickel and magnesium in the form of their sulfates, chlorides, acetates, and nitrates, preferably in the form of their nitrates. In order to prevent undesirable hydrolysis and to promote precipitation, it is recommended to provide an excess of free acid in the mixed salt solution.

The mixed salt solution is transferred separately but simultaneously together with an aqueous solution of a basic precipitant to a support suspended in water. The compound which serves as precipitant is an aqueous solution of a basic compound, in particular an aqueous alkali metal carbonate, alkali metal hydrogen carbonate, alkali metal hydroxide, ammonium hydroxide, or ammonium carbonate solutions. Mixtures of these solutions can also be used. An aqueous solution containing $Na_2CO_3$ and/or $NaHCO_3$ is particularly suitable. The precipitant should have a pH of 7.5 to 13, preferably 8 to 12, most preferably 9 to 11.

The aqueous solution contains 0.1 to 4.0, in particular 0.6 to 3.0, preferably 1.6 to 2.4, equivalents of basic compound/liter of solution. Very good results are achieved with aqueous solutions containing 0.3 to 1.5, preferably 0.8 to 1.2, mols of alkali metal carbonate/liter of solution.

In order to ensure that precipitation is as complete as possible and, at the same time, obtain a particularly homogeneous coprecipitate consisting of basic nickel and magnesium compounds, the basic compound is used in slight excess of the amount required for complete precipitation of the nickel and magnesium. Precipitation is achieved by adding and mixing the mixed salt solution and the precipitating agent separately but simultaneously, either continuously or discontinuously, to the support material suspended in water.

The precipitation of the coprecipitate consisting of basic nickel and magnesium compounds is achieved by comparatively slow addition of the mixed salt solution and the precipitating agent. The precipitation time should be at least 10, in particular at least 15, preferably at least 20 minutes. During precipitation, a constant pH value in the range of 6 to 8.5, in particular 6.5 to 7.8, is maintained. Fluctuations in the pH value should be kept to a minimum. Precipitation is conducted at temperatures above 80°, in particular 90° to 110°, preferably 95° to 105° C.

The coprecipitate contains magnesium and nickel corresponding to a molar ratio of 0.02 to 0.25:1, in particular 0.03 to 0.2:1, preferably 0.035 to 0.1:1. It is removed from the mother liquor on completion of precipitation, e.g. by decanting and/or filtering. When the coprecipitate is subsequently washed with water, not only the constituents in the solution, e.g. $Na^+$ and $NO^-_3$, but also the basic magnesium compounds contained in the coprecipitate are washed out. The reduction in magnesium causes the molar ratio of magnesium to nickel to fall. Washing is carried out at relatively high temperature of 60° to 90°, in particular 65° to 85°, preferably 70° to 80° C. The washing process must be sufficiently long. It should be at least 60, in particular at least 80, preferably at least 90 minutes. If desired, the washed catalyst mixture can be fashioned into shapes. Time-tested processes, for example continuous extrusion, can be used for this purpose.

Drying is performed in stages at elevated temperatures, preferably at increasing temperatures. It has proven satisfactory to dry at temperatures of 50° to 120°, in particular 55° to 100°, preferably 60° to 90° C. using conventional processes, such as placing the material to be dried in a fixed or moving bed, e.g. a fluidized bed. The catalyst mixture is reduced using hydrogen or hydrogen-containing gas mixtures at temperatures of 260° to 400°, in particular 280° to 360° C.

A special feature of the process according to the invention is its wide range of applications. It can be used, if desired, both for preparing saturated primary or secondary amines and for preparing unsaturated primary amines. If the intention is to prepare primary amines, the catalytic hydrogenation of the nitriles is performed in the presence of ammonia at temperatures of 80° to 200°, in particular 100° to 180°, preferably 120° to 170° C.

According to a special variation of the process, saturated primary amines are prepared by a two-stage catalytic hydrogenation of the nitriles in the presence of ammonia; temperatures of 80° to 140°, in particular 110° to 130° C., are used initially. For the second step, temperatures of 140° to 180°, in particular 150° to 170° C., have been found satisfactory.

Unsaturated primary amines can be prepared particularly successfully by performing the catalytic hydrogenation of the nitriles in the presence of ammonia at temperatures of 100° to 140°, in particular 110° to 130° C. In order to prepare either saturated or unsaturated primary amines, catalytic hydrogenation is performed at a pressure of 1.0 to 6.0, in particular 1.5 to 5.0, preferably 2.0 to 4.0 MPa. It is recommended that the reaction be carried out with the addition of ammonia; this improves the selectivity of the reaction and suppresses dissociation reactions resulting, for example, in the release of ammonia. 2% to 10% by weight of ammonia, based on the nitrile, is normally added to the reaction.

The preparation of secondary amines requires different conditions from those used in the synthesis of saturated and unsaturated primary amines. In general, the temperatures required are higher. Performing the catalytic hydrogenation of the nitriles at temperatures of 160° to 250°, in particular 170° to 240°, preferably 180° to 220° C. has proved successful. The pressure is 0.1 to 5.0, in particular 0.2 to 3.0, preferably 0.3 to 2.0 MPa. The addition of ammonia is unnecessary. During the preparation of secondary amines, it is particularly advantageous to continuously remove from the reaction the ammonia released during the catalytic hydrogenation of the nitriles. This is accomplished, for example, by passing a stream of hydrogen through the reaction which forces the ammonia out.

The process according to the invention is particularly suitable for discontinuous operation but it can also be performed continuously or semi-continuously. In the discontinuous mode, the nickel-containing support catalyst, corresponding to 0.05% to 2.0%, in particular 0.08% to 1.0%, preferably 0.1% to 0.5% by weight of nickel, based on the to nitrile, is used.

Suitable starting materials are nitriles having 6 to 24 carbon atoms, in particular straight-chain and/or branched aliphatic nitriles having 8 to 22 carbon atoms, preferably straight-chain and/or branched aliphatic nitriles having 10 to 22 carbon atoms. The process according to the invention is particularly successful in the hydrogenation of nitriles which are derived from higher natural fatty acids, for example lauric acid, palmitic acid, stearic acid and oleic acid, in particular mixtures of these nitriles or industrial-grade nitriles. Such an industrial-grade material is tallow fatty acid nitrile which consists primarily of nitriles of stearic acid, palmitic acid and oleic acid.

The following Examples illustrate the invention but are not limitative.

EXAMPLE 1

Preparation of unsaturated primary tallow fatty amine 400 g of distilled tallow fatty acid nitrile is placed in a 1 liter, stirrer-equipped autoclave rinsed with nitrogen. A catalyst enveloped in higher fatty amines is used, which contains, based on the total catalyst mass, about 64% by weight of fatty amines, 19.5% by weight of nickel, and 36.34 g of support (kieselguhr) per mole of nickel. Mg and Ni are present in a molar ratio of 0.04:1. The catalyst has an active nickel metal surface area of 120 m$^2$/g of nickel and a BET total surface area of 220 m$^2$/g of catalyst (calculated without the enveloping covering of fatty amine). 80% of the BET total surface area is formed by pores having a radius $r_p \leq 2.5$ nm (25 Å). The filtration time of the catalyst is 2.33 min.

4.1 g of the catalyst and 24 g of NH$_3$ are added. Then hydrogen is introduced until a pressure of 2.1 MPa is reached and the reaction mixture is heated with stirring to the reaction temperature (125° C). The reaction pressure (3.1 MPa) is set and maintained by continuous addition of hydrogen.

Comparative Example 1

Preparation of unsaturated tallow fatty amine

As specified in Example 1, 400 g of distilled tallow fatty acid nitrile is placed in a 1 liter, stirrer-equipped autoclave rinsed with nitrogen. 10 g of a Raney nickel catalyst, containing about 60% by weight of nickel based on the total mass of the catalyst and enveloped in distearylamine, as well as 24 g of NH$_3$, are added. Then hydrogen is introduced until a pressure of 2.1 MPa is reached and the reaction mixture is heated with stirring to the reaction temperature (125° C.). The reaction pressure (3.1 MPa) is set and maintained by continuous addition of hydrogen.

Comparative Example 2

Preparation of unsaturated tallow fatty amine

As specified in Example 1, 400 g of distilled tallow fatty acid nitrile is placed in a 1 liter, stirrer-equipped autoclave rinsed with nitrogen. 4.35 g of a commercially available support catalyst (recommended for the hydrogenation of nitriles) containing 20.7% by weight of Ni, 0.1% by weight MgO, about 3.2% by weight of SiO$_2$, and about 3.5% by weight of Al$_2$O$_3$, being covered with distearylamine, and having a filtration time of 6.74 min, is added along with 24 g of NH$_3$. Then hydrogen is introduced until a pressure of 2.1 MPa is reached and the reaction mixture is heated with stirring to the reaction temperature (125° C.). The reaction pressure (3.1 MPa) is set and maintained by the continuous addition of hydrogen.

The reaction conditions and the composition of the reaction products obtained are summarized in Table 1.

TABLE 1

|  | Example 1 | Comparative experiment 1 | Comparative experiment 2 |
| --- | --- | --- | --- |
| Reaction conditions |  |  |  |
| Nickel related to starting material* | 0.2 wt % | 1.5 wt % | 0.225 wt % |
| Temperature | 125° C. | 125° C. | 125° C. |
| Pressure | 3.1 MPa | 3.1 MPa | 3.1 MPa |
| NH$_3$ related to starting material | 6 wt % | 6 wt % | 6 wt % |
| Total reaction time** | 270 min. | 270 min. | 270 min. |
| H$_2$ uptake | 170 min. | 240 min. | 210 min. |
| Composition of the reaction product in wt % |  |  |  |
| Primary amines | 96.5 | 96.4 | 95.8 |
| Secondary amines | 1.9 | 2.1 | 2.5 |
| Tertiary amines | 0.9 | 0.9 | 0.8 |
| Non-amines | 0.7 | 0.6 | 0.9 |
| Iodine value (g J$_2$/100 g) | 52 | 31 | 51 |

*Starting material: tallow fatty acid nitrite with a nitrite content of >99.5 wt % (determined by GC), iodine number: 56.9 (g J$_2$/100 g), 0.01 wt % water, 0.028 wt % amide nitrogen in addition to traces of Na, S, Cl and P.
**including 40 min. heating time Analysis of the reaction product The hydrogenated product is analyzed for its iodine value amine content and non-amine content.

The total amine content is determined by titration using HCl dissolved in isopropanol. To determine the amounts of secondary and tertiary amines, the primary amines are first converted into the corresponding azomethines (Schiff's base) with salicylaldehyde, and the remaining secondary and tertiary amines are then determined by titration using HCl dissolved in isopropanol. To determine the tertiary amines, the primary and secondary amines are first converted into the corresponding derivatives with acetic anhydride, and the remaining tertiary amines determined by titration using HClO$_4$ dissolved in acetic acid.

The non-amine content is determined by gas chromatographic (GC) analysis of the reaction product from which all amines have been previously removed using an acidic ion exchanger. This is an analytical method based on ASTM D 2082-82. The non-amines are, for example, alcohols, carboxylic acids, amides, and esters, but not unreacted nitrile, as confirmed by infrared spectroscopic examination (with the exception of Comparative Experiments 5, 6 and 7.)

EXAMPLE 2

Preparation of dodecylamine 200 g of dodecylnitrile is placed in a 1 liter, stirrer-equipped autoclave rinsed with nitrogen. 3.08 g of the catalyst described in Example 1 and 20 g of NH$_3$ are added.

Then hydrogen is introduced until a pressure of 1.6 MPa is reached and the reaction mixture is heated with stirring to the reaction temperature (140° C). The reaction pressure (2.6 MPa) is maintained by the continuous addition of hydrogen. The reaction is complete after 60 minutes. The reaction produces primary dodecylamine in a yield >96% of the theoretical value. The non-amine content is <1% by weight.

EXAMPLE 3

Preparation of saturated primary amines 400 g of the tallow fatty acid nitrile used in Example 1 is placed in a 1 liter, stirrer-equipped autoclave rinsed with nitrogen. 6.15 g of the catalyst described in Example 1 (corresponding to 0.3% by weight of Ni based on the tallow fatty acid nitrile) and 24 g of $NH_3$ are added. Then hydrogen is introduced and the reaction mixture is heated with stirring to the reaction temperature. The reaction takes place in two stages:

1st Stage:

| | |
|---|---|
| Temperature | 130° C. |
| Pressure | 3.1 MPa |
| Reaction time | 100 min. |

After the 1st stage, the autoclave is depressurized and rinsed with hydrogen, thus removing any $NH_3$ still present. Subsequently, hydrogen is again introduced and the reaction mixture is heated with stirring to the reaction temperature of the 2nd stage.

2nd Stage:

| | |
|---|---|
| Temperature | 150° |
| Pressure | 3.1 MPa |
| Reaction time ca. | 140 min. |

The 2-stage reaction of the tallow fatty acid nitrile (iodine value 56.9 (g $I_2$/100 g)) results in a reaction product with a primary amine content $\leq 93\%$ by weight and a non-amine content $\geq 0.7\%$ by weight. The iodine value is <5 (g $I_2$/100 g).

EXAMPLE 4

Preparation of secondary saturated tallow fatty amine (distearylamine)

500 g of the tallow fatty acid nitrile of Example 1 is placed in a 1 liter autoclave equipped with a stirrer and rinsed with nitrogen. 4.76 g of a catalyst enveloped in higher fatty amines is added.

Based on the total catalyst mass, the catalyst contains about 63% by weight of fatty amines, 21% by weight of nickel, 36.3 g of support (kieselguhr) per mole of nickel; Mg and Ni are present in a molar ratio of 0.055:1. The catalyst has an active nickel metal surface area of 141 $m^2$/g of nickel and a BET total surface area of 310 $m^2$/g of catalyst (calculated without the enveloping fatty amine covering); 83% of the BET total surface area is formed by pores having a radius $r_p \leq 2.5$ nm (25 Å).

The hydrogen required for the reaction is passed continuously and in excess via a dip tube provided with a distribution device through the catalyst-containing suspension with stirring. At the same time the waste gas containing unreacted hydrogen, and ammonia formed by the reaction, is drawn off. The addition of hydrogen and the removal of waste gas are balanced so that, during the heating period and the subsequent reaction, a pressure of 0.3 MPa is maintained. The temperature is raised to 200° C. over a period of 45 minutes and the reaction continued for 4 hours.

Comparative Example 3

Preparation of secondary saturated tallow fatty amine (distearylamine)

500 g of the tallow fatty acid nitrile used in Example 1 is placed in a 1 liter, stirrer-equipped autoclave rinsed with nitrogen. 5.56 g of a commercially available catalyst are added. The catalyst is recommended for conversion of nitriles to secondary fatty amines, and contains, according to the manufacturer, 18% by weight of nickel, about 2% by weight of copper, about 7% by weight of support and, in addition, primarily a secondary amine as an enveloping protective covering. The subsequent procedure is the same as specified in Example 4. However, the reaction product still contains considerable amounts of unsaturated secondary amines, as the iodine number in Table 2 indicates.

Comparative Example 4

Preparation of secondary saturated tallow fatty amine (distearylamine)

The procedure is the same as specified in Comparative Example 3, the only difference being that 27.8 g of the catalyst of comparative Example 1 is used. The reaction conditions and the composition of the reaction products obtained are described in Table 2.

TABLE 2

| | Example 4 | Comparative experiment 3 | Comparative experiment 4 |
|---|---|---|---|
| Reaction conditions | | | |
| Nickel related to starting material* | 0.2 wt % | 0.2 wt % | 1.0 wt % |
| Temperature | 200° C. | 200° C. | 200° C. |
| Pressure | 0.3 MPa | 0.3 MPa | 0.3 MPa |
| Total reaction time** | 285 min. | 285 min. | 285 min. |
| Composition of the reaction product in wt % | | | |
| Primary amines | 0.7 | 6.1 | 1.4 |
| Secondary amines | 94.0 | 91.7 | 91.8 |
| Tertiary amines | 4.6 | 1.7 | 4.6 |
| Non-amines | 0.7 | 0.5 | 2.2 |
| Iodine value (g $J_2$/100 g) | 0.7 | 27.0 | 3.9 |

TABLE 2-continued

|  | Example 4 | Comparative experiment 3 | Comparative experiment 4 |
| --- | --- | --- | --- |

*Starting material: tallow fatty acid nitrile as specified in table 1
**including 45 min. heating time

EXAMPLE 5

Preparation of unsaturated primary tallow fatty amine 400 g of distilled tallow fatty acid nitrile with a nitrile content (determined by GC) of >99.5% by weight, an iodine value of 51.7 (g $I_2$/100 g), and containing 0.01% by weight of water, 0.02% by weight of amide nitrogen (as well as traces of Na, S, Cl and P), are added together with 3.81 g of the catalyst described in Example 4 (corresponding to 0.2% by weight of Ni based on the tallow fatty acid nitrile) and 24 g of $NH_3$. The subsequent procedure is the same as specified in Example 1. After 160 minutes, hydrogen absorption is complete. The reaction product exhibits the following composition (in % by weight).

| Primary amines | 96.6 |
| --- | --- |
| Secondary amines | 2.1 |
| Tertiary amines | 0.8 |
| Non-amines | 0.5 |
| Iodine value (g $I_2$/100 g) | 49 |

EXAMPLE 6

Preparation of unsaturated primary tallow fatty amine

A continuously extruded catalyst not enveloped in fatty amine is used. Based on the total catalyst mass, the catalyst contains 59.7% by weight Ni, 33.2 g of support (kieselguhr) per mol of nickel, and Mg and Ni in a molar ratio of 0.03:1. It has an active nickel metal surface area of 129 $m^2$/g of nickel and a BET total surface area of 286 $m^2$/g of catalyst. 74.4% of the BET total surface area is formed by pores having a radius $r_p \leq 2.5$ nm (25 Å), 73% of the BET total surface area is formed by pores having a radius $r_p = 1.5$ to 2.5 nm (15 to 25 Å), and 64% of the BET total surface area is formed by pores having a radius $r_p = 1.8$ to 2.5 nm (18 to 25 Å). 1.34 g of this continuously extruded catalyst, corresponding to 0.2% by weight of nickel, based on the tallow fatty acid nitrile starting material is placed in a 1 liter, stirrer-equipped autoclave rinsed with nitrogen, and reduced in size by crushing using a pestle.

Subsequently, 400 g of distilled tallow fatty acid nitrile, having a nitrile content (determined by gas chromatography) of 99.5% by weight, and an iodine value of 55 (g $I_2$/100 g), are added with 24 g of $NH_3$. This is followed by the same procedure as specified in Example 1. Hydrogen absorption is complete after 210 minutes. This higher value compared with Example 1 is attributable to the fact that the catalyst does not have such fine particles as those used in Example 1.

The reaction product exhibits the following composition (in % by weight):

| Primary amines | 95.9 |
| --- | --- |
| Secondary amines | 2.6 |
| Tertiary amines | 0.6 |
| Non-amines | 0.9 |
| Iodine value (g $I_2$/100 g) | 47.5 |

EXAMPLE 7

Preparation of unsaturated primary oleyl amine 500 g of distilled oleyl nitrile with a nitrile content (determined by gas chromatography) of about 99.5% by weight, an iodine value of 92.8 (g $I_2$/100 g), and containing 0.02% by weight amide nitrogen, is placed in a 1 liter, stirrer-equipped autoclave rinsed with nitrogen. A catalyst enveloped in higher fatty amines is used which, based on the total catalyst mass, contains about 63% by weight of fatty amines, 21% by weight of nickel, about 36 g of support (kieselguhr) per mole of nickel, and Mg and Ni in a molar ratio of 0.053:1. The catalyst has an active nickel metal surface area of 125 $m^2$/g of nickel and a BET total surface area of 273 $m^2$/g catalyst (without the enveloping fatty amine), 71% of the BET total surface area being formed by pores having a radius $r_p \leq 2.5$ nm (25 Å).

4.76 g of this catalyst (corresponding to 0.2% by weight of Ni, based on the oleyl nitrile) and 30 g of $NH_3$ are added. The same procedure is then followed as specified in Example 1, the only difference being that the mixture is heated to the desired reaction temperature within 30 min. Hydrogen absorption is complete after 320 min.

Comparative Example 5

Preparation of unsaturated primary oleyl amine

The same procedure is followed as described in Example 7, except that 5 g of the catalyst described in Comparative Example 2 are used. The reaction conditions and the composition of the reaction products obtained according to Example 7 and Comparative Example 5 are summarized in Table 3.

TABLE 3

|  | Example 7 | Comparative experiment 5 |
| --- | --- | --- |
| Reaction conditions |  |  |
| Nickel related to starting material | 0.2 wt % | 0.2 wt % |
| Temperature | 125° C. | 125° C. |
| Pressure | 3.1 MPa | 3.1 MPa |
| $H_2$ uptake | 320 min. | 335 min. |
| Total reaction time* | 365 min. | 365 min. |
| Composition of the reaction product in wt % |  |  |
| Primary amines | 96.6 | 43.5 |
| Secondary amines | 1.7 | 0.3 |
| Tertiary amines | 0.6 | 0.1 |
| Non-amines | 1.1 | 56.4** |
| Iodine value (g $J_2$/100 g) | 88.5 | 89.7 |

*including 30 min. heating time
**mainly unreacted starting material

EXAMPLE 8

Preparation of unsaturated primary tallow fatty amine 400 g of the distilled tallow fatty acid nitrile of Example 6 is placed in a 1 liter, stirrer-equipped autoclave rinsed with nitrogen. 3.81 g of the catalyst described in Example 7, as well as 24 g of NH$_3$, is added. The subsequent procedure is the same as specified in Example 1, the only difference being that the mixture is heated to the reaction temperature within 30 min. The reaction time is 165 min.

Comparative Example 6

Preparation of unsaturated primary tallow fatty amine

The procedure is the same as specified in Example 8, except that 1.33 g of the catalyst described in Comparative Example 1 (corresponding to 0.2% by weight of nickel based on the tallow fatty acid nitrile) is used. The reaction time is 165 min.

Comparative Example 7

Preparation of unsaturated primary tallow fatty amine

The procedure is the same as specified in Example 8, the only difference being that 4.0 g of the catalyst described in Comparative Example 2 (corresponding to 0.2% by weight of nickel based on the tallow fatty acid nitrile) is used. The reaction time is 165 min.

The reaction conditions and the composition of the reaction products obtained according to Example 8 and Comparative Examples 6 and 7 are summarized in Table 4.

TABLE 4

|  | Example 8 | Comparative experiment 6 | Comparative experiment 7 |
|---|---|---|---|
| Reaction conditions |  |  |  |
| Nickel related to starting material | 0.2 wt % | 0.2 wt % | 0.2 wt % |
| Temperature | 125° C. | 125° C. | 125° C. |
| Pressure | 3.1 MPa | 3.1 MPa | 3.1 MPa |
| Start of H$_2$ uptake | 107° C. | 104° C. | 124° C. |
| Total reaction time* | 195 min. | 195 min. | 195 min. |
| Composition of the reaction product in wt % |  |  |  |
| Primary amines | 94.4 | 76.8 | 21.4 |
| Secondary amines | 2.4 | 1.5 | 1.8 |
| Tertiary amines | 0.8 | 0.8 | 0.6 |
| Non-amines | 1.4 | about 20** | about 75** |
| Iodine value (g J$_2$/100 g) | 51.5 | 52.6 | 53.6 |

*including 30 min. heating time
**mainly unreacted starting material

While only a limited number of specific embodiments of the present invention have been expressly disclosed, it is, nonetheless, to be broadly construed, and not to be limited except by the character of the claims appended hereto.

What we claim is:

1. A process for the preparation of amines by catalytic hydrogenation of nitriles comprising the reaction of said nitriles with hydrogen at elevated temperatures in the presence of a supported catalyst containing coprecipitated Mg and Ni in a molar ratio of 0.015–0.060 to 1, and 17.0 to 60.0 g of a water-insoluble support per tool of Ni, said Ni having an active nickel metal surface of said catalyst of 110 to 180 m$^2$/g of said Ni, and 65% to 97% of the BET surface area of said catalyst being formed by pores having a radius $r_p \leq 2.5$ nm.

2. The process of claim 1 wherein ammonia is present.

3. The process of claim 1 wherein said catalyst has a BET total surface area of 160 to 450 m$^2$/g.

4. The process of claim 3 wherein said total surface area is 200 to 350 m$^2$/g.

5. The process of claim 1 wherein said molar ratio is 0.022 to 0.055.

6. The process of claim 1 wherein said support is selected from the group consisting of silicates, aluminum oxide, silicon dioxide, kieselguhr, and mixtures thereof.

7. The process of claim 1 wherein said support has a particle size of 1 to 30 μm.

8. The process of claim 2 wherein said amines are primary amines and said elevated temperature is 80° to 200° C.

9. The process of claim 8 wherein said elevated temperature is 120° to 170° C.

10. The process of claim 2 wherein said amine is a saturated amine and said process is carried out in a first step and a second step, said first step being at a first temperature of 80° to 140° C. and said second step being at a second temperature of 140° to 180° C.

11. The process of claim 10 wherein said first temperature is 110° C. to 130° C. and said second temperature is 150° to 180° C.

12. The process of claim 1 wherein said amine is a primary amine and said hydrogenation takes place at a hydrogenation pressure of 1.0 to 6.0 MPa.

13. The process of claim 12 wherein said hydrogenation pressure is 2.0 to 4.0 MPa.

14. The process of claim 1 wherein said amine is a secondary amine and said hydrogenation is carried out at a hydrogenation temperature of 160° to 250° C.

15. The process of claim 14 wherein said hydrogenation temperature is 180° to 220° C.

16. The process of claim 1 wherein said amine is a secondary amine and said hydrogenation is carried out at a hydrogenation pressure of 0.1 to 5.0 MPa.

17. The process of claim 16 wherein said hydrogenation pressure is 0.3 to 2.0 MPa.

18. The process of claim 16 wherein ammonia released by said reaction is removed.

19. The process of claim 1 wherein said catalyst is present in a catalyst amount of 0.05% to 2.0% by weight of said nickel, based on said nitrile.

20. The process of claim 19 wherein said catalyst amount is 0.1% to 0.5% by weight of said nickel, based on said nitrile.

21. The process of claim 1 wherein said nitriles have 6 to 24 carbon atoms.

22. The process of claim 21 wherein said nitriles has 10 to 22 carbon atoms.

23. The process of claim 22 wherein said nitriles are aliphatic.

24. The process of claim 1 wherein 60% to 95% of said

BET surface area is formed by pores having $r_p$=1.5 to 2.5 nm.

25. The process of claim 24 wherein 35% to 85% of said BET surface area is formed by pores having $r_p$=1.8 to 2.5 nm.

26. The process of claim 1 wherein there is 25 to 50 g of said support per mol of said Ni.

27. The process of claim 1 wherein said active nickel metal surface is 130 to 150 m²/g.

28. The process of claim 1 wherein said Mg and said Ni are coprecipitated from a salt solution thereof.

29. The process of claim 28 wherein said salt solution contains 10 to 100 g Ni per liter.

30. The process of claim 28 wherein said salt solution contains an amount of Mg corresponding to 0.2 to 15 g of MgO per liter.

* * * * *